US009150820B2

(12) United States Patent
Hamamatsu et al.

(10) Patent No.: US 9,150,820 B2
(45) Date of Patent: Oct. 6, 2015

(54) SURFACTANT COMPOSITION

(71) Applicant: KAO CORPORATION, Tokyo (JP)

(72) Inventors: Mayu Hamamatsu, Wakayama (JP);
Takafumi Nishi, Wakayama (JP);
Masazumi Iwashita, Wakayama (JP);
Tomoaki Sasa, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/369,665

(22) PCT Filed: Dec. 27, 2012

(86) PCT No.: PCT/JP2012/083929
§ 371 (c)(1),
(2) Date: Jun. 27, 2014

(87) PCT Pub. No.: WO2013/100075
PCT Pub. Date: Jul. 4, 2013

(65) Prior Publication Data
US 2014/0371331 A1   Dec. 18, 2014

(30) Foreign Application Priority Data

Dec. 28, 2011 (JP) .................. 2011-287194
Dec. 28, 2011 (JP) .................. 2011-290108
Dec. 7, 2012 (JP) .................. 2012-268235

(51) Int. Cl.
| | |
|---|---|
| *A61K 8/86* | (2006.01) |
| *A61Q 5/00* | (2006.01) |
| *A61Q 19/00* | (2006.01) |
| *C07C 41/03* | (2006.01) |
| *C07C 43/10* | (2006.01) |
| *C11D 1/825* | (2006.01) |
| *C11D 1/72* | (2006.01) |

(52) U.S. Cl.
CPC ............ *C11D 1/8255* (2013.01); *A61K 8/86* (2013.01); *A61Q 5/00* (2013.01); *A61Q 19/00* (2013.01); *C07C 41/03* (2013.01); *C11D 1/825* (2013.01); *A61K 2800/594* (2013.01); *A61K 2800/596* (2013.01); *A61K 2800/5922* (2013.01); *C11D 1/72* (2013.01); *C11D 1/721* (2013.01)

(58) Field of Classification Search
CPC ............ A61K 8/86; A61K 2800/5922; A61K 2800/594; A61K 2800/596; A61Q 5/00; A61Q 19/00; C07C 41/03; C07C 43/10; C07C 43/135; C11D 1/825; C11D 1/8255; C11D 1/72; C11D 1/721; C07B 61/00
See application file for complete search history.

(56) References Cited

U.S. PATENT DOCUMENTS

| | | |
|---|---|---|
| 4,086,279 A | 4/1978 | Langdon et al. |
| 5,057,627 A | 10/1991 | Edwards |
| 2002/0035238 A1 | 3/2002 | Nakamura et al. |
| 2005/0271610 A1 | 12/2005 | Neuss et al. |
| 2009/0239958 A1* | 9/2009 | Sakanishi et al. ............ 516/9 |

FOREIGN PATENT DOCUMENTS

| | | |
|---|---|---|
| EP | 2 163 237 A2 | 3/2010 |
| JP | 2-42037 A | 2/1990 |
| JP | 11-315043 A | 11/1999 |
| JP | 2011-114720 A | 4/2001 |
| JP | 2009-227583 A | 10/2009 |
| JP | 2011-16774 A | 1/2011 |
| JP | 2011-88867 A | 5/2011 |
| JP | 2013-14560 A | 1/2013 |
| JP | 2013-100265 A | 5/2013 |

OTHER PUBLICATIONS

International Search Report issued in PCT/JP2012/083929, mailed on Feb. 5, 2013.
Extended European Search Report, issued May 15, 2015, for European Application No. 12863633.9.

* cited by examiner

*Primary Examiner* — Brian P Mruk
(74) *Attorney, Agent, or Firm* — Birch, Stewart, Kolasch & Birch, LLP

(57) ABSTRACT

The present invention provides a surfactant composition containing a polyglycerol alkyl ether which is capable of exhibiting a high emulsification performance for silicone oils compounded in cosmetics, detergents, etc., by using a natural alcohol derived from oils and fats as a raw material thereof, a process for producing the surfactant composition in an effective manner, and a use of the surfactant composition. The present invention relates to [1] a surfactant composition including a specific polyglycerol monoalkyl ether (1) and a specific polyglycerol dialkyl ether (2), a mass ratio of [(1)/(2)] being from 65/35 to 75/25; [2] a process for producing the surfactant composition; [3] an emulsifier composition including the surfactant composition; and [4] a detergent composition including the surfactant composition.

17 Claims, No Drawings

SURFACTANT COMPOSITION

FIELD OF THE INVENTION

The present invention relates to a surfactant composition containing a polyglycerol alkyl ether having a specific composition and a process for producing the surfactant composition, and an emulsifier composition and a detergent composition containing the surfactant composition.

BACKGROUND OF THE INVENTION

It is known that a surfactant composition containing a polyglycerol monoalkyl ether and a polyglycerol dialkyl ether is suitably used in the applications such as cosmetics and detergents because the composition can exhibit a good emulsification effect for forming an emulsion having an excellent stability with time.

For example, Patent Document 1 discloses a polyglycerol alkyl ether-type nonionic surfactant having a polyglycerol monoalkyl ether content of 75% by weight or more and a polyglycerol dialkyl ether content of 5% by weight or less.

Patent Document 2 discloses a cosmetic composition or detergent composition containing a polyglycerol 2-ethylhexyl ether in which an average number of 2-ethylhexyl groups added to a polyglycerol is 1.5 or more.

Also, Patent Document 3 discloses a two-part hair dye composition having a gentle effect on skin which is free from sagging of foams for a period from application to hair up to rinsing because the hair dye composition can maintain a good foaming property even at a low temperature. The two-part hair dye composition disclosed in Patent Document is constituted of an alkaline agent and a hydrogen peroxide agent at least one of which contains a polyglycerol alkyl ether having a specific composition including 75% by weight or more of a polyglycerol monoalkyl ether (monoalkyl compounds), 5% by weight or less of a polyglycerol dialkyl ether (dialkyl compounds) and 20% by weight or less of a polyglycerol.

CITATION LIST

Patent Literature

Patent Document 1: JP 2009-227583A
Patent Document 2: JP 2011-16774A
Patent Document 3: JP 2011-88867A

SUMMARY OF THE INVENTION

However, both of the surfactant compositions disclosed in Patent Documents 1 and 2 which contain the polyglycerol monoalkyl ether and the polyglycerol dialkyl ether are obtained from a branched-chain aliphatic alcohol as an alcohol derived from petrochemical feedstock. In recent years, with the increase in awareness of environmental issues, there is an increasing demand for replacement of the petrochemical feedstock that will cause global warming with carbon-neutral feedstock such as typically natural oils and fate.

On the other hand, in Patent Document 3, although the surfactant composition containing the polyglycerol monoalkyl ether and the polyglycerol dialkyl ether as disclosed therein is used in a two-part hair dye composition, there is no description concerning an emulsification effect on silicone oils.

The present invention aims at providing a surfactant composition containing a polyglycerol alkyl ether which is capable of exhibiting a high emulsification performance for silicone oils compounded in cosmetics, detergents, etc., by using a natural alcohol derived from oils and fats as a raw material thereof, a process for producing the surfactant composition in an effective manner, and a use of the surfactant composition.

The present inventors have found that the conventional problems can be solved by using a surfactant composition containing a polyglycerol monoalkyl ether and a polyglycerol dialkyl ether which are derived from a polyglycerol having a specific polymerization degree, at a specific mass ratio.

That is, the present invention relates to the following aspects [1] to [5].

[1] A surfactant composition including a compound represented by the formula (1) and a compound represented by the formula (2), a mass ratio of the compound represented by the formula (1) to the compound represented by the formula (2) [(1)/(2)] being from 65/35 to 75/25:

$$R^1O \mathrm{+\!\!-\!\!C_3H_6O_2\!\!-\!\!+}_n H \qquad (1)$$

wherein $R^1$ is a linear alkyl group having 10 to 14 carbon atoms; $[C_3H_6O_2]$ is a glycerol unit; n represents an average polymerization degree of $[C_3H_6O_2]$, and is a number of from 2.3 to 10; and a total content of a triglycerol monoalkyl ether, a tetraglycerol monoalkyl ether and a pentaglycerol monoalkyl ether in the compound represented by the formula (1) is 75% by mass or more; and

$$R^2O \mathrm{+\!\!-\!\!C_3H_6O_2\!\!-\!\!+}_m R^2 \qquad (2)$$

wherein two $R^2$ groups are each independently a linear alkyl group having 10 to 14 carbon atoms; $[C_3H_6O_2]$ is a glycerol unit; and m represents an average polymerization degree of $[C_3H_6O_2]$, and is a number of from 1 to 10.

[2] A process for producing the surfactant composition as described in the above aspect [1], including the following steps (I), (II) and (III):

Step (I): subjecting glycerol to dehydration condensation in the presence of an alkaline catalyst to obtain a glycerol polymer;

Step (II): removing glycerol, or glycerol and diglycerol from the glycerol polymer obtained in the step (I) to obtain a polyglycerol having a glycerol content of 5% by mass or less or having a glycerol content of 5% by mass or less and a diglycerol content of 40% by mass or less; and Step (III): subjecting the polyglycerol obtained in the step (II) to addition reaction with a glycidyl ether in the presence of a γ-alumina catalyst containing titanium in an amount of from 600 to 5000 ppm, or an alkaline catalyst.

[3] A process for producing the surfactant composition as described in the above aspect [1], including the step of reacting an alcohol with glycidol in the presence of a simple metal salt of a rare earth element.

[4] An emulsifier composition including the surfactant composition as described in the above aspect [1].

[5] A detergent composition including the surfactant composition as described in the above aspect [1].

Effect of the Invention

In accordance with the present invention, there can be provided a surfactant composition containing a polyglycerol alkyl ether which is capable of exhibiting a higher emulsification performance for silicone oils compounded in cosmetics as compared to conventional surfactant compositions containing such a polyglycerol alkyl ether, a process for producing the surfactant composition in an effective manner, as well as an emulsifier composition and a detergent composition containing the surfactant composition.

DETAILED DESCRIPTION OF THE INVENTION

[Surfactant Composition]

The surfactant composition of the present invention includes a compound represented by the aforementioned formula (1) (i.e., a polyglycerol monoalkyl other) and a compound represented by the aforementioned formula (2) (i.e., a polyglycerol dialkyl ether), in which a mass ratio of the compound represented by the formula (1) to the compound represented by the formula (2) [(1)/(2)] is from 65/35 to 75/25.

The surfactant composition of the present invention may also contain a polyglycerol within a predetermined range as described below.

<Polyglycerol Monoalkyl Ether>

The polyglycerol monoalkyl ether contained in the surfactant composition of the present invention has a structure represented by the following formula (1).

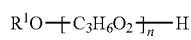
(1)

In the formula (1), $R^1$ is a linear alkyl group having 10 to 14 carbon atoms; $[C_3H_6O_2]$ is a glycerol unit; and n represents an average polymerization degree of $[C_3H_6O_2]$, and is a number of from 2.3 to 10. The average polymerization degree (n) as used herein means the value calculated from the below-mentioned calculation formula (5) based on values measured by the method as described in Examples hereinlater. Also, from the viewpoint of a good emulsification performance, n is preferably a number of from 2.3 to 6 and more preferably from 3 to 5.

In addition, the total content of a triglycerol monoalkyl ether, a tetraglycerol monoalkyl ether and a pentaglycerol monoalkyl ether in the polyglycerol monoalkyl ether is 75% by mass or more, preferably 80% by mass or more, and more preferably from 85 to 98% by mass.

The linear alkyl group having 10 to 14 carbon atoms as $R^1$ in the formula (1) is preferably a linear alkyl group having 12 to 14 carbon atoms from the viewpoint of a high emulsifying power of the resulting composition, etc.

Examples of specific structures of $[C_3H_6O_2]_n$ in the formula (1) are one or more structures selected from the group consisting of those structures represented by the following formulae (1-1) to (1-5).

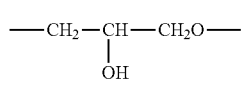
(1-1)
(1-2)
(1-3)

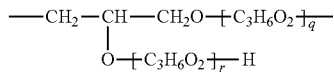
(1-4)

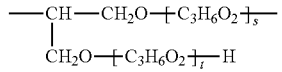
(1-5)

In the above formulae, q, r, a and t are respectively an integer of 1 or more, and $[C_3H_6O_2]$ has the same meaning as defined above.

Meanwhile, the total content of a triglycerol monoalkyl ether, a tetraglycerol monoalkyl ether and a pentaglycerol monoalkyl ether in the polyglycerol monoalkyl ether may be determined by a gas chromatographic method (GC method).

<Polyglycerol Dialkyl Ether>

The polyglycerol dialkyl ether contained in the surfactant composition of the present invention has a structure represented by the following formula (2).

(2)

In the formula (2), two, R groups are each independently a linear alkyl group having 10 to 14 carbon atoms; $[C_3H_6O_2]$ is a glycerol unit; and m represents an average polymerization degree of $[C_3H_6O_2]$, and is a number of from 1 to 10. From the viewpoint of a good emulsification performance, m is preferably a number of from 3 to 7 and more preferably from 4 to 6. The average polymerization degree (m) as used herein means the value calculated from the below-mentioned calculation formula (5) based on values measured by the method as described in Examples hereinlater.

Examples of specific structures of $[C_3H_6O_2]_m$ are the same as those specific structures described with respect to the above $[C_3H_6O_2]_n$.

The linear alkyl group having 10 to 14 carbon atoms as $R^2$ in the formula (2) is preferably a linear alkyl group having 12 to 14 carbon atoms from the viewpoint of a high emulsifying power of the resulting composition.

Also, the total content of a tetraglycerol dialkyl ether, a pentaglycerol dialkyl ether and a hexaglycerol dialkyl ether in the polyglycerol dialkyl ether represented by the formula (2) is 75% by mass or more, preferably 80% by mass or more, and more preferably from 85 to 99% by mass.

In the surfactant composition of the present invention, from the viewpoint of a high emulsifying power of the resulting composition, the mass ratio of the polyglycerol monoalkyl ether represented by the formula (1) to the polyglycerol dialkyl ether represented by the formula (2) [(1)/(2)] is required to lie within the range of from 65/35 to 75/25, and is preferably from 65/35 to 73/27, and more preferably 65/35 to 70/30.

<Polyglycerol>

The surfactant composition of the present invention may also contain a polyglycerol within a predetermined range. The polyglycerol contained in the composition has the effect of further stabilizing an emulsion liquid membrane and enhancing a emulsification stability of the resulting composition. The content of the polyglycerol in the surfactant composition is preferably from 1 to 60% by mass, more preferably from 10 to 50% by mass, still more preferably from 20 to 45% by mass, and even still more preferably from 20 to 40% by mass from the viewpoint of enhancing an emulsification performance of the resulting composition and a productivity thereof.

In the formula (3), $[C_3H_6O_2]$ is a glycerol unit; k represents an average polymerization degree of $[C_3H_6O_2]$, and is a number of from 1 to 10; and a total content of a diglycerol, a triglycerol and a tetraglycerol in the polyglycerol is 75% by mass or more. The average polymerization degree (k) as used herein means the value calculated from the below-mentioned calculation formula (6) based on values measured by the method as described in Examples hereinlater.

Examples of specific structures of $[C_3H_6O_2]_k$ are the same as those specific structures described with respect to the above $[C_3H_6O_2]_n$.

The polyglycerol preferably has a Gardner value of 3 or less, more preferably 2 or less and still more preferably 1 or less, and even still more preferably has an APHA value of 200 or less from the viewpoint of a good quality of the polyglycerol and polyglycerol alkyl ether (improvement in hue thereof. The Gardner value and the APHA value of the polyglycerol may be measured by the method described in Examples below.

[Process for Producing Surfactant Composition]

The process for producing the surfactant composition of the present invention is not particularly limited, and there may be mentioned the following production processes (1) and (2). Of these production processes, from the viewpoint of enhancing a productivity, preferred is the production process (1), and more preferred is the production process (1) including the step (III) in which a titanium-containing γ-alumina catalyst is used.

<Production Process (1)>

The production process (1) is a process for producing the surfactant composition of the present invention which includes the following steps (I), (II) and (III).

Step (I): subjecting glycerol to dehydration condensation in the presence of an alkaline catalyst to obtain a glycerol polymer;

Step (II): removing glycerol, or glycerol and diglycerol from the glycerol polymer obtained in the step (I) to obtain a polyglycerol having a glycerol content of 5% by mass or less or having a glycerol content of 5% by mass or less and a diglycerol content of 40% by mass or less; and Step (III): subjecting the polyglycerol obtained in the step (II) to addition reaction with a glycidyl ether in the presence of a γ-alumina catalyst containing titanium in an amount of from 600 to 5000 ppm, or an alkaline catalyst.

<Step (I)>

In the step (I), glycerol is subjected to dehydration condensation in the presence of an alkaline catalyst to obtain a glycerol polymer.

(Alkaline Catalyst)

As the alkaline catalyst, there may be mentioned at least one compound selected from the group consisting of hydroxides, carbonates, bicarbonates, alkoxides and hydrides of alkali metals or alkali earth metals.

Examples of the alkali metals include lithium, sodium and potassium. Of these alkali metals, sodium and potassium are preferred from the viewpoints of easiness of handling and a high reactivity.

Examples of the alkali earth metals include magnesium, calcium, strontium and barium. Of these alkali earth metals, preferred is barium.

From the viewpoints of a high reactivity and a good economy, the alkaline catalyst is preferably at least one compound selected from the group consisting of hydroxides, carbonates, bicarbonates and alkoxides of alkali metals or alkali earth metals, more preferably at least one compound selected from the group consisting of hydroxides, carbonates and bicarbonates of alkali metals or alkali earth metals, and still more preferably at least one compound selected from the group consisting of sodium hydroxide, potassium hydroxide, sodium carbonate; potassium carbonate and barium hydroxide.

The amount of the alkaline catalyst used in the step (1) is preferably from 0.1 to 5 mol %, more preferably from 0.1 to 3 mol %, still more preferably from 0.2 to 2 mol %, and even still more preferably from 0.2 to 1 mol %, in view of enhancing a reactivity, reducing a burden upon neutralization after completion of the reaction or upon removal of the catalyst, and improving a hue of the polyglycerol.

(Raw Glycerol)

The glycerol used as a raw material (hereinafter also referred to as a "raw glycerol") preferably has a carbonyl value of from 0.001 to 3.5 μmol/g, more preferably from 0.01 to 3.5 μmol/g, still more preferably from 0.1 to 3.5 μmol/g, even still more preferably from 0.1 to 3.0 μmol/g, further even still more preferably from 0.1 to 2.0 μmol/g, further even still more preferably from 0.1 to 1.5 μmol/g, and further even still more preferably from 0.1 to 1.0 μmol/g, from the viewpoint of reducing a burden on purification of the raw glycerol and improving a hue of the resulting polyglycerol.

The reason why the polyglycerol having an excellent hue can be obtained from the above raw glycerol is not clearly determined, but is considered to be that when using the glycerol whose carbonyl value lies within the above-specified range, decomposition or polymerization of a carbonyl compound contained in the raw glycerol can be suppressed.

The carbonyl value as used herein means the number of μmol of the carbonyl compound (such as a ketone and an aldehyde) contained in 1 g of the sample (glycerol). More specifically, the carbonyl value is the value measured by the method described in Examples below.

The carbonyl value of the raw glycerol can be controlled within the above-specified range by subjecting the raw glycerol to distillation, hydrogen reduction, adsorption treatment, etc.

Also, the raw glycerol preferably has a conductivity of from 0 to 100 μS/cm, more preferably from 0 to 50 μS/cm, still more preferably from 0 to 30 μS/cm, even still more preferably from 0 to 20 μS/cm, and further even still more preferably from 0 to 10 μS/cm from the viewpoints of enhancing a reactivity of the dehydration condensation reaction and improving a hue of the resulting polyglycerol. The conductivity of glycerol as used herein means a conductivity of a 50% glycerol aqueous solution as measured at 20° C., more specifically, is the value measured by the method described in Examples below.

The conductivity of the raw glycerol can be controlled within the above-specified range by subjecting the raw glycerol to distillation, hydrogen reduction, adsorption, desalting treatment, etc.

The raw glycerol may be in the form of either purified glycerol or crude glycerol subjected to no treatments such as deodorization, decoloring, desalting, adsorption, ion exchange, etc., as long as the carbonyl value thereof lies within the above-specified range. From the viewpoint of reducing a burden on purification step of the raw glycerol, the crude glycerol is preferably used. The crude glycerol as used herein is glycerol obtained by the below-mentioned transesterification reaction or hydrolysis reaction of oils and fats which are not subjected to treatments such as deodorization, decoloring, desalting, adsorption, ion exchange, etc.

The raw glycerol may be produced by hydrolysis of oils and fats, transesterification reaction of oils an fats with an alcohol, or chemical synthesis. From the viewpoints of economy and a well-controlled carbonyl value of the resulting glycerol, the raw glycerol is preferably produced by subjecting oils and fats and an alcohol to transesterification reaction.

[Transesterification Reaction]

Examples of the oils and fats used in the transesterification reaction include vegetable oils and fats such as coconut oils, palm oils, palm kernel oils, soybean oils, rapeseed oils, sunflower oils, cottonseed oils, peanut oils and algae oils; and animal oils and fats such as beef tallow, lard and fish oils. These oils and fats may be in the form of a purified or refined product.

The alcohol used in the transesterification reaction is preferably a lower alcohol having 1 to 5 carbon atoms. Examples of the alcohol include methanol, ethanol, propanol and butanol. Of these alcohols, from the industrial viewpoints of low costs and facilitated recovery, preferred is methanol.

The transesterification reaction between the oils and fats and the alcohol is preferably conducted in the presence of a solid catalyst from the viewpoints of reducing a burden on purification of the raw glycerol and improving a hue of the resulting polyglycerol. The solid catalyst as used herein means a catalyst having an alcoholysis reaction activity which is insoluble in the reaction solution. The solid catalyst is preferably a solid acid catalyst from the viewpoint of enhancing a selectivity to glycerol.

Examples of the solid acid catalyst include at least one material selected from the group consisting of niobic acid, silica-alumina, silica-titania, silica-zirconia, titania-zirconia, aluminum phosphate, an aluminum orthophosphate catalyst, iron phosphate, aluminum sulfate, sulfate ion-carrying zirconia, sulfate ion-carrying titania, antimony pentafluoride-carrying silica-alumina, acid clay, kaolin, montmorillonite, a fluorinated sulfone resin, synthetic zeolite and a cation exchange resin. Of these solid acid catalysts, preferred is the aluminum orthophosphate catalyst having a less number of strong acid sites and a high selectivity to glycerol.

The aluminum orthophosphate catalyst is preferably in the form of an alkyl phosphonic acid/aluminum phosphate composite catalyst obtained by introducing an alkyl group into an aluminum phosphate catalyst.

The reaction type of the transesterification reaction may be either a batch type or a continuous type. In addition, the transesterification reaction may be carried out using a vessel type reactor equipped with a stirrer or a fixed bed reactor filled with a catalyst. From the viewpoint of reducing a burden on purification of the reaction product, the transesterification reaction is preferably carried out using the fixed bed reactor which needs no procedure for separating the catalyst therefrom.

The molar ratio of the raw material alcohol to the oils and fats used in the transesterification reaction (in terms of the value calculated assuming that all of the oils and fats are constituted of a triglyceride) is controlled such that an amount of the raw material alcohol used is preferably 1.5 times or more, more preferably 2 times or more and still more preferably 5 times or more a stoichiometric amount of the alcohol required in the reaction from the viewpoint of attaining a good reaction rate.

Also, from the viewpoint of suppressing an amount of the raw material alcohol recovered and conducing the reaction in an economical manner, the molar ratio of the raw material alcohol to the oils and fats used in the transesterification reaction is controlled such that an amount of the raw material alcohol used is preferably 50 times or less, more preferably 30 times or less and still more preferably 15 times or less a stoichiometric amount of the alcohol required in the reaction.

Therefore, from these viewpoints, the molar ratio of the raw material alcohol to the oils and fats used in the transesterification reaction is controlled such that an amount of the raw material alcohol used is preferably from 1.5 to 50 times, more preferably from 2 to 30 times and still more preferably from 5 to times a stoichiometric amount of the alcohol required in the reaction.

The amount of the solid acid catalyst used in the transesterification reaction is preferably 1% by mass or more, more preferably 3% by mass or more, and still more preferably 5% by mass or more on the basis of the oils and fats from the viewpoint of enhancing a reaction efficiency. Also, from the viewpoint of maintaining a sufficient suspension condition by stirring, the amount of the solid acid catalyst used in the transesterification reaction is preferably 20% by mass or less, more preferably 17% by mass or less, and still more preferably 15% by mass or less on the basis of the oils and fats.

Therefore, from these viewpoints, the amount of the solid acid catalyst used in the transesterification reaction is preferably from 1 to 20% by mass, more preferably from 3 to 17% by mass, and still more preferably from 5 to 15% by mass on the basis of the oils and fats.

The reaction temperature used in the transesterification reaction is preferably from 50 to 220° C., more preferably from 60 to 200° C., still more preferably from 80 to 200° C., and even still more preferably from 130 to 200° C. from the viewpoints of enhancing a reaction efficiency and suppressing production of by-products.

Also, the reaction pressure is preferably from 0.1 to 10 MPa, more preferably from 0.5 to 8 MPa and still more preferably from 2 to 6 MPa from the viewpoint of enhancing a reaction efficiency.

The liquid hourly space velocity (LHSV) of the transesterification reaction based on the oils and fats when conducting the reaction in a continuous manner using a fixed bed reactor is preferably 0.02/hr or more, more preferably 0.1/hr or more, and still more preferably 0.2/hr or more from the viewpoints of enhancing a productivity per a unit capacity of the reactor and conducting the reaction in an economical manner. Also, from the viewpoint of attaining a sufficient reaction rate, the LHSV of the transesterification reaction based on the oils and fats is preferably 2.0/hr or less, more preferably 1.0/hr or less, and still more preferably 0.7/hr or less. Incidentally, the above LHSV means an inverse number of a time required for passing the reaction raw materials through the catalyst layer.

(Dehydration Condensation)

In the step (I), the glycerol is subjected to dehydration condensation to obtain a glycerol polymer.

The reaction temperature used in the step (I) is preferably from 180 to 270° C., more preferably from 200 to 260° C., still more preferably from 210 to 250° C., and even still more preferably from 220 to 250° C. from the viewpoints of suppressing deterioration in reactivity and enhancing a productivity and a quality of the resulting polyglycerol.

The conversion rate of glycerol in the step (I) is preferably from 20 to 90%, more preferably from 20 to 85%, and still more preferably from 20 to 75% from the viewpoint of a high performance upon derivatization into a surfactant. The conversion rate of glycerol as used herein means a proportion of a mass of glycerol consumed in the reaction to a mass of glycerol used in the reaction, and may be measured by the method described in Examples below.

The reaction time in the step (I) may vary depending upon the reaction conditions, and is preferably from 0.1 to 20 h, more preferably from 1 to 15 h, and still more preferably from 1 to 10 h from the viewpoints of enhancing a quality of the resulting polyglycerol and a productivity.

The pressure used in the reaction of the step (I) is preferably from 30 to 101.3 kPa, more preferably from 30 to 90 kPa, and still more preferably from 30 to 80 kPa, from the viewpoint of removing water produced by the reaction from the reaction system to enhance a reaction efficiency. In addition, the water may also be removed from the reaction system by flowing an inert gas such as nitrogen and argon through the reaction system at an optional flow rate.

After completion of the step (I) and before initiation of the below-mentioned step (II), a step of neutralizing the alkaline catalyst using a neutralization agent is preferably subjected from the viewpoint of a good quality of the resulting polyglycerol. The neutralization step corresponds to a removal step of the catalyst.

Examples of the neutralization agent include organic acids such as acetic acid, lactic acid and citric acid; and inorganic acids such as phosphoric acid, sulfuric acid and hydrochloric acid. Of these neutralization agents, from the viewpoints of good economy and a good handling property, preferred are acetic acid, lactic acid, phosphoric acid, sulfuric acid and hydrochloric acid, and more preferred are lactic acid, sulfuric acid and phosphoric acid.

In addition, from the viewpoint of a good influence on derivatization reaction from the polyglycerol as the raw material into a surfactant such as a polyglycerol fatty acid ester and a polyglycerol alkyl ether, adsorption treatment with an ion exchange resin, a synthetic absorbent and so on may be subjected to remove the alkaline catalyst and neutralized salts thereof.

<Step (II)>

In the step (II), glycerol, or glycerol and diglycerol, are removed from the glycerol polymer obtained in the step (I) to obtain a polyglycerol having a glycerol content of 5% by mass or less, or having a glycerol content of 5% by mass or less and a diglycerol content of 40% by mass or less.

In the step (II), the glycerol polymer obtained in the step (I) is subjected to simple distillation, etc., to remove glycerol therefrom until the content of glycerol therein on the basis of a whole amount of the polyglycerol reaches 5% by mass or less (in terms of an area % in GC), or after removing glycerol from the glycerol polymer until the content of glycerol therein on the basis of a whole amount of the polyglycerol reaches 5% by mass or less, the obtained reaction solution is then subjected to molecular distillation, etc., to further remove diglycerol from the reaction solution until the content of diglycerol therein on the basis of a whole amount of the polyglycerol reaches 40% by mass or less (in terms of an area % in GC), whereby it is possible to obtain a polyglycerol having a glycerol content of 5% by mass or less, or having a glycerol content of 5% by mass or less and a diglycerol content of 40% by mass or less.

The method of controlling the content of glycerol or the content of diglycerol is not particularly limited. For example, the glycerol polymer may be subjected to a distillation step such as simple distillation, thin-film type distillation and molecular distillation to remove a whole or part of the residual glycerol or diglycerol, so that the composition distribution or average polymerization degree of the polyglycerol can be controlled to the given suitable range.

In addition, the glycerol or diglycerol thus recovered by the above distillation may be reused as a raw material for production of polyglycerol.

For this reason, the method including the step (II) after completion of the step (1) may be conducted as a method for producing the diglycerol.

The distillation of the unreacted glycerol is preferably conducted at a vacuum degree of from 1 Pa to 7 kPa and a distilling temperature of from 130 to 250° C., more preferably at a vacuum degree of from 10 Pa to 4 kPa and a distilling temperature of from 130 to 230° C., and still more preferably at a vacuum degree of from 10 Pa to 1.5 kPa and a distilling temperature of from 130 to 190° C., from the viewpoint of suppressing occurrence of the dehydration condensation reaction during the distillation. The glycerol or diglycerol thus recovered by the distillation is preferably reused as a raw material for production of polyglycerol from the viewpoint of a high productivity. Meanwhile, the distillation of the unreacted glycerol is preferably conducted by simple distillation.

The distillation of the diglycerol is preferably conducted at a vacuum degree of from 1 Pa to 0.7 kPa and a distilling temperature of from 180 to 300° C., and more preferably at a vacuum degree of from 1 Pa to 0.2 kPa and a distilling temperature of from 180 to 280° C., from the viewpoint of a good quality of the resulting polyglycerol and diglycerol. In addition, from the viewpoint of improving a quality of the diglycerol, the distillation of the diglycerol is preferably conducted after the distillation of the unreacted glycerol.

The distillation of the diglycerol may be conducted using a simple distillation, distillation using an apparatus such as a thin-film type distillation apparatus or a molecular distillation apparatus. From the viewpoint of a good quality of the diglycerol, the distillation of the diglycerol is preferably conducted using a thin-film type distillation apparatus or a molecular distillation apparatus.

In the thin-film type distillation apparatus or molecular distillation apparatus, as the method of forming a thin film, there may be mentioned a falling method, a rising liquid film method, a wiper method, an agitating method, a rotating method, a centrifugal method, etc.

The falling method is the method in which a polyglycerol as a raw material to be distilled is allowed to naturally fall along a heated inner wall surface of the apparatus to form a thin film thereon. The rising liquid film method is the method in which a gas is introduced from a bottom of the apparatus to push up a liquid film and thereby form a thin film therein.

The wiper method is the method in which a polyglycerol as a raw material to be distilled is allowed to naturally fall along an inner wall surface of the apparatus and further wiped on the inner wall surface using a wiper blade to form a thin film thereon. The agitating method is the method in which a polyglycerol supplied in the apparatus is stirred using a scraper or the like to form a thin film thereof.

The rotating method is the method in which a polyglycerol as a raw material is cast over a surface of a rotating disc to form a thin film thereon, or the method in which the polyglycerol is supplied between an outer cylinder and a rotating inner cylinder to form a thin film therein. The centrifugal method is the method in which a thin film is formed by a centrifugal force on opposite wall surfaces of an outer cylinder and an inner cylinder. Of these methods, from the viewpoint of a facility used, preferred are a falling method, a wiper method and an agitating method.

The polyglycerol obtained by any of the above methods and diglycerol obtained by distillation of the polyglycerol may be subjected to one or more purification steps such as activated carbon treatment, active clay treatment and ion exchange resin treatment, if required, to further improve a quality thereof.

From the viewpoint of further improving a hue or an odor, they are preferably subjected to activated carbon treatment, ion exchange resin treatment or both the treatments. The diglycerol obtained by the above methods preferably has a Gardner value of 3 or less and more preferably 1 or less, and still more preferably has an APHA value of 100 or less from the viewpoint of a good quality of the diglycerol and polyglycerol alkyl ether (improvement in hue thereof). The Gardner value and the APHA value of the diglycerol may be measured by the method described in Examples below.

<Step (III)>

In the step (III), the polyglycerol obtained in the step (II) is subjected to addition reaction with a glycidyl ether in the presence of a γ-alumina catalyst containing titanium in an amount of from 600 to 5000 ppm (a) or in the presence of an alkaline catalyst (b).

(a) Method Using Titanium-Containing γ-Alumina Catalyst

[Titanium-Containing γ-Alumina Catalyst]

The γ-alumina catalyst containing titanium in an amount of from 600 to 5000 ppm (hereinafter also referred to merely as a "titanium-containing γ-alumina catalyst") is in the form of a dehydrated product of aluminum hydroxide having a spinel structure or a defect spinel structure which contains titanium therein.

The content of titanium in the titanium-containing γ-alumina catalyst is from 600 to 5000 ppm (on the mass basis) from the viewpoint of enhancing a productivity and a reactivity, and is preferably from 600 to 1300 ppm and more preferably from 1000 to 1100 ppm.

The content of aluminum in the titanium-containing γ-alumina catalyst is preferably from 40 to 55% by mass, more preferably from 45 to 53% by mass, and still more preferably from 49 to 50% by mass from the viewpoints of enhancing a reactivity and a productivity and maintaining a crystal structure thereof.

The average particle size of the titanium-containing γ-alumina catalyst is not particularly limited, and is preferably from 100 to 500 μm, more preferably from 100 to 300 am, and still more preferably from 100 to 150 μm from the viewpoint of enhancing a reaction rate.

The average particle size as used herein means a particle size corresponding to a cumulative value of 50% in a particle size distribution measured by a laser diffusion scattering method.

The titanium-containing γ-alumina catalyst may be produced by the conventionally known methods (for example, the method described in JP 2007-511343A).

(Addition Reaction Conditions)

The temperature of the addition reaction between the polyglycerol and the glycidyl ether is preferably from 80 to 300° C., more preferably from 100 to 250° C., still more preferably from 140 to 240° C., even still more preferably from 160 to 230° C., further even still more preferably from 180 to 220° C., and most preferably from 180 to 210° C. from the viewpoint of enhancing a reactivity and a productivity.

The reaction time of the above addition reaction is from about 2 to about 20 h, preferably from 2 to 10 h, more preferably from 2 to 8 h, and still more preferably from 2 to 6 h from the viewpoints of enhancing a productivity and reducing residual raw materials in the resulting product.

In the above addition reaction, from the viewpoints of suppressing hydrolysis of the glycidyl ether and enhancing a productivity, the content of water in the reaction system is preferably from 0 to 1.0% by mass, more preferably from 0.005 to 0.5% by mass, and still more preferably from 0.01 to 0.3% by mass.

More specifically, it is preferred that the raw materials (polyglycerol and glycidyl ether) previously subjected to dehydration treatment are used, and the dehydration treatments for the polyglycerol and glycidyl ether both are conducted at a temperature of from 60 to 130° C. under a pressure of from 0.01 to 5 kPa, in particular, from 0.01 to 1.5 kPa from the viewpoint of avoiding occurrence of thermal decomposition of the reaction raw materials.

Further, after charging the reaction raw materials and the titanium-containing γ-alumina catalyst into the reaction apparatus, the contents of the reaction apparatus may be subjected to dehydration treatment at a temperature of 120° C. or higher under a pressure of 0.05 kPa or less.

In the above addition reaction, the titanium-containing γ-alumina catalyst is preferably used in an amount of from 0.05 to 20% by mass, more 16 preferably from 0.1 to 10% by mass, still more preferably from 0.2 to 7% by mass, and even still more preferably from 0.5 to 6% by mass on the basis of the polyglycerol from the viewpoints of enhancing a reactivity, a productivity and easiness of handling.

From the viewpoint of suppressing side reactions, the above addition reaction is preferably conducted in an inert gas atmosphere, and more preferably in an atmosphere of a nitrogen gas or an argon gas. The reaction pressure is preferably from 0.010 to 2.0 MPa, and more preferably from 0.10 to 1.0 MPa from the viewpoint of enhancing a productivity.

The above addition reaction may be conducted by a batch reaction method. The batch reaction method as used herein means the reaction method in which the reaction raw materials are charged into a constant capacity reaction vessel, and the obtained reaction product is withdrawn from the reaction vessel in the course of the reaction or after completion of the reaction.

All of the polyglycerol, the titanium-containing γ-alumina catalyst and the glycidyl ether may be charged into the batch reaction apparatus from an initial time of the reaction and reacted with each other. Alternatively, the polyglycerol and the titanium-containing γ-alumina catalyst may be first previously charged into the reaction apparatus, and then the glycidyl ether may be added (dropwise) into the reaction apparatus to react with the previously charged components.

In the addition reaction, from the viewpoint of suppressing hydrolysis of the glycidyl ether, it is preferred that after charging a solution containing the polyglycerol and the titanium-containing γ-alumina catalyst into the batch reaction apparatus, the solution is heated to a reaction temperature at which a whole amount of the glycidyl ether is added at one time (one-time addition) to the reaction apparatus to allow the contents of the reaction apparatus to react with each other.

Meanwhile, the one-time addition as used herein means that a whole amount of the glycidyl ether used in the reaction is added to the reaction system as short as possible. The addition time is preferably within 100 min, more preferably within 60 min, still more preferably within 45 min, and even still more preferably within 30 min.

The method of separating the titanium-containing γ-alumina catalyst after completion of the addition reaction is not particularly limited. From the viewpoint of reducing a viscosity of the resulting reaction product to enhance a handling property thereof, there is preferably used the method in which the reaction product is heated to a temperature of from 80 to 120° C. and subjected to filtration at that temperature to separate the titanium-containing γ-alumina catalyst therefrom. In addition, in order to reduce a viscosity of the reaction product, various solvents (such as water and a lower monohydric alcohol) or filtration assistants (such as diatomaceous earth, cellulose-based assistants and active clay) may be added to the reaction product, followed by separating the titanium-containing γ-alumina catalyst from the resulting mixture by filtration.

(b) Method Using Alkaline Catalyst (Alkaline Catalyst)

Specific examples and preferred examples of the alkaline catalyst used in the step (III) are the same as those of the alkaline catalyst used in the step (I).

(Addition Reaction Conditions)

In the above method, the addition reaction between the polyglycerol and the glycidyl ether is preferably conducted by using the alkaline catalyst in an amount of more than 0.02% by mass and not more than 0.8% by mass. When the amount of the alkaline catalyst used lies within the above-specified range, it is possible to prevent defects such as deterioration in reactivity and occurrence of coloration of the reaction solution. The alkaline catalyst is preferably used in an amount of from 0.03 to 0.7% by mass, more preferably from 0.03 to 0.6% by mass, still more preferably from 0.03 to 0.5% by mass, even still more preferably from 0.03 to 0.4% by mass, and further even still more preferably from 0.03 to 0.3% by mass, and most preferably from 0.04 to 0.2% by mass on the basis of the polyglycerol.

The reaction temperature is preferably from 180 to 250° C. When the reaction temperature falls within the above-specified range, the reaction is free from disadvantages such as poor production efficiency owing to deterioration in reactivity, accelerated hydrolysis reaction of the glycidyl ether, and concurrence of dehydration condensation of the polyglycerol, which result in failure to obtain the polyglycerol alkyl ether as aimed.

The reaction temperature is preferably from 180 to 240° C., more preferably from 185 to 230° C., and still more preferably from 190 to 230° C. from the viewpoints of enhancing a productivity and suppressing a hydrolysis reaction.

The reaction time is preferably from 0.1 to 20 h, more preferably from 1 to 10 h, still more preferably from 1 to 8 h, and even still more preferably from 1 to 6 h from the viewpoints of enhancing a productivity and reducing the residual raw materials.

The addition reaction is preferably conducted in an inert gas atmosphere, in particular, in an atmosphere of an argon gas or a nitrogen gas from the viewpoint of suppressing side reactions.

The pressure used in the addition reaction is preferably from 0.010 to 2.0 MPa, and more preferably from 0.10 to 1.0 MPa from the viewpoint of enhancing a productivity.

The above addition reaction may be conducted by a batch method. All of the polyglycerol, the alkaline catalyst and the glycidyl ether may be charged into the batch reaction apparatus from an initial time of the reaction and reacted with each other. Alternatively, the polyglycerol and the alkaline catalyst may be first previously charged into the reaction apparatus, and then the glycidyl ether may be added (dropwise) into the reaction apparatus to react with the previously charged components.

In the addition reaction, from the viewpoint of suppressing a hydrolysis reaction of the glycidyl ether, it is preferred that after charging a solution containing the polyglycerol and the alkaline catalyst into the batch reaction apparatus, the solution is heated to a reaction temperature at which a whole amount of the glycidyl ether is added to the reaction apparatus at one time to allow the contents of the reaction apparatus to react with each other. The addition time is preferably within 100 min similarly to the method using the titanium-containing γ-alumina catalyst (a).

In the above method, after completion of the reaction, the alkaline catalyst is preferably neutralized by adding an organic acid such as acetic acid, lactic acid and citric acid, or an inorganic acid such as phosphoric acid, sulfuric acid and hydrochloric acid to the reaction solution. In addition, the thus neutralized reaction solution is preferably subjected to adsorption treatments using an ion exchange resin, a synthetic adsorbent, etc., according to the requirements, to remove the alkaline catalyst and its neutralized salts therefrom.

In the method using the titanium-containing γ-alumina catalyst (a) and the method using the alkaline catalyst (b) which is to be conducted in the step (III), an organic solvent may also be used, if required.

Examples of the organic solvent include an ether-based solvent containing no active hydrogen, a ketone-based solvent, an aromatic hydrocarbon-based solvent, an amide-based solvent and a sulfoxide-based solvent. Of these organic solvents, from the viewpoint of enhancing a productivity of the polyglycerol alkyl ether and a selectivity to a 1:1 adduct of the polyglycerol with the glycidyl ether, preferred is an ether-based solvent containing no active hydrogen, and more preferred is a compound represented by the following general formula (4).

$$R^3\text{—O—}[(PO)_p/(EO)_q]\text{—}R^4 \quad (4)$$

wherein $R^3$ and $R^4$ are respectively an alkyl group having 1 to 8 carbon atoms; PO and EO represent a propyleneoxy group and an ethyleneoxy group, respectively; p is a number of moles of PO added, and q is a number of moles of EO added, and p and q are respectively a number of from 0 to 10 with the proviso that a sum of p and q is from 2 to 20, and the order of addition of PO and EO is optional; and the slash mark "/" means that a configuration of addition of PO and EO may be either a block form or a random form.

Meanwhile, the "active hydrogen" represents a hydrogen atom contained in a hydroxyl group (—OH), a carboxyl group (—COOH), an amino group (—NH$_2$) or a thiol group (—SH), and the expression "containing no active hydrogen" means that the hydrogen atom contained in these functional groups is substituted with a hydrocarbon group or the like.

In the above general formula (4), $R^3$ and $R^4$ are each independently an alkyl group having 1 to 8 carbon atoms, and is preferably an alkyl group having 1 to 3 carbon atoms, and more preferably a methyl group from the viewpoint of enhancing a productivity of the polyglycerol alkyl ether.

In the above general formula (4), a sum of p and q is from 2 to 20, preferably from 2 to 10, more preferably from 3 to 5, and still more preferably from 3 to 4 from the viewpoint of enhancing a productivity of the polyglycerol alkyl ether.

Examples of the compound represented by the above general formula (4) include diethylene glycol dimethyl ether, triethylene glycol dimethyl ether, tetraethylene glycol dimethyl ether, pentaethylene glycol dimethyl ether, diethylene glycol diethyl ether, triethylene glycol diethyl ether, tetraethylene glycol diethyl ether and pentaethylene glycol diethyl ether. Of these compounds, from the viewpoint of enhancing a productivity of the polyglycerol alkyl ether, preferred are diethylene glycol dimethyl ether, triethylene glycol dimethyl ether, tetraethylene glycol dimethyl ether or pentaethylene glycol dimethyl ether, and more preferred are triethylene glycol dimethyl ether or tetraethylene glycol dimethyl ether.

The boiling point of the ether-based solvent containing no active hydrogen is preferably a temperature not lower than the reaction temperature used in the present invention from the viewpoint of enhancing a productivity of the polyglycerol alkyl ether. The boiling point as used herein means a normal boiling point, i.e., a temperature at which a saturation vapor pressure is identical to 1013.25 hPa (1 atm).

Specifically, the boiling point of the ether-based solvent containing no active hydrogen is preferably from 180 to 500° C. more preferably from 180 to 400° C. and still more preferably from 180 to 300° C. from the viewpoint of reducing a burden on facilities.

The amount of the ether-based solvent containing no active hydrogen used is preferably from 1 to 500% by mass, more preferably from 20 to 200% by mass, still more preferably from 30 to 150% by mass, even still more preferably from 50 to 150% by mass, and further even still more preferably from 60 to 140% by mass on the basis of 100% by mass of the polyglycerol from the viewpoint of enhancing a productivity of the polyglycerol alkyl ether.

<Production Process (2)>

The production process (2) is a process for producing the surfactant composition of the present invention (containing a polyglycerol alkyl ether) by reacting an alcohol with a glycidol in the presence of a simple metal salt of a rare earth element (hereinafter also referred to as a "rare earth-based catalyst").

The simple metal salt as used herein means a metal salt of a primary compound except for a double salt and a complex salt.

As the simple metal salt of a rare earth element, there may be usually used an inorganic acid salt and/or an organic acid salt. From the viewpoints of realizing a high-selectivity addition reaction and enhancing a conversion rate of alcohols, the suitable inorganic acid salt is a perchloric acid salt, and the suitable organic acid salt is an organic sulfonic acid salt.

Examples of the preferred rare earth element constituting the simple metal salt include scandium, yttrium, and lanthanoids such as lanthanum, cerium, praseodymium, neodymium, samarium, europium, gadolinium, terbium, dysprosium, holmium, erbium, thulium, ytterbium and lutetium. Of these rare earth elements, more preferred are scandium, lanthanum, samarium, europium, erbium, lutetium and ytterbium, still more preferred are scandium, lanthanum, samarium and ytterbium, and especially preferred are lanthanum and/or samarium.

Examples of an organic sulfonic acid constituting the organic sulfonic acid salt include trifluoromethanesulfonic acid, methanesulfonic acid, toluenesulfonic acid and dodecylbenzenesulfonic acid. Of these organic sulfonic acids, from the viewpoints of realizing a high-selectivity addition reaction and enhancing a conversion rate of alcohols, preferred is trifluoromethanesulfonic acid.

(Reaction Conditions)

The amount of the simple metal salt of a rare earth element used in the reaction is preferably from 0.001 to 0.2 mol, more preferably from 0.002 to 0.1 mol, and still more preferably from 0.005 to 0.05 mol per 1 mol of the alcohol from the viewpoint of a good balance between a reaction rate and economy.

The reaction between the alcohol and the glycidol is an exothermic reaction, and therefore the alcohol and the glycidol are preferably gradually reacted with each other by adding the glycidol to the alcohol in a continuous dropwise manner or by slit addition of the glycidol to the alcohol, while stirring the alcohol.

The reaction temperature may be appropriately selected according to the kind of alcohol used, etc., and is from 0 to 200° C., preferably from 30 to 170° C., more preferably from 50 to 150° C., and still more preferably from 80 to 130° C. from the viewpoints of a reaction time, a reaction efficiency, a yield, a quality of the resulting product, etc.

[Surfactant Composition]

The surfactant compositions obtained by the above production processes (1) and (2) can exhibit an extremely high emulsifying power against silicone oils generally used in cosmetics or perfumery. In addition, these surfactant compositions can also exhibit an extremely high emulsifying power against hydrocarbon-based oil-soluble substances generally used in cosmetics or perfumery. Therefore, the surfactant composition of the present invention can be used in the extensive applications as an emulsifier composition such as a detergent composition, a cosmetic composition and a composition for clothing.

[Detergent Composition]

The detergent composition of the present invention contains the surfactant composition of the present invention.

The surfactant composition of the present invention may be used by itself as the detergent composition of the present invention, or the detergent composition of the present invention may be prepared by mixing the surfactant composition of the present invention with the other surfactant than the compounds represented by the above formulae (1) and (2) and/or water, if required.

Examples of the other surfactant used in the detergent composition of the present invention include an anionic surfactant, a nonionic surfactant, an amphoteric surfactant and a cationic surfactant.

Specific examples of the anionic surfactant include polyoxyethylene alkyl ether sulfuric acid salts, alkyl sulfate fatty acid salts, fatty acid salts, phosphoric acid ester salts, sulfosuccinic acid-based surfactants, sulfosuccinamate-based surfactants, polyoxyalkylene alkylamide-ether sulfuric acid salts, monoglyceride sulfuric acid salts, olefin sulfonic acid salts, alkane sulfonic acid salts, acylated isethionic acid salts, acylated amino acid salts, polyoxyalkylene alkyl ether phosphoric acid salts and polyoxyalkylene alkyl ether acetic acid salts, polyoxyethylene alkylamide ether Specific examples of the nonionic surfactant include alkyl polyglucosides, sucrose fatty acid esters, polyglycerol fatty acid esters, polyoxyalkylene alkyl ethers, fatty acid alkanol amides, alkyl amine oxides and fatty acid polyhydric alcohol esters.

Specific examples of the amphoteric surfactant include amide betaine-based surfactants, amide amino acid-based surfactants, carbobetaine-based surfactants, sulfobetaine-based surfactants, amide sulfobetaine-based surfactants, imidazolium betaine-based surfactants and phosphobetaine-based surfactants.

Specific examples of the cationic surfactant include quaternary ammonium salts.

Examples of the detergent composition of the present invention include a skin detergent such as a facial cleanser and a body shampoo, a hair detergent such as a shampoo, and a hard surface detergent such as a dish detergent. The detergent composition of the present invention may further contain optional components according to the applications as aimed.

Examples of the optional components include conditioning components including oil agents such as higher alcohols having 12 to 18 carbon atoms, silicones and silicone derivatives, lanolin, squalene, hydrocarbons, protein derivatives and polyethylene glycol fatty acid esters; and cationized celluloses, cationized guar gum, cation polymers and cationic group-containing copolymers.

Examples of the other components usually used in the detergent composition include a water-soluble polymer, a chelate agent, an antiseptic agent, an antioxidant, a pH controller, a pigment and a perfume.

The detergent composition of the present invention may be produced by an ordinary method. The dosage form or configuration of the detergent composition of the present invention is not particularly limited, and the detergent composition of the present invention may have any optional shape such as a liquid, a paste, a cream, a solid, a powder, etc. Of these configurations, preferred are a liquid, a paste and a cream, and more preferred is a liquid. In the case where the detergent composition is in the form of a liquid, water is preferably used as a liquid medium.

[Other Emulsifier Compositions]

The emulsifier compositions containing the surfactant composition according to the present invention can be used in the extensive applications as a cosmetic composition such as a skin cosmetic and a hair cosmetic, and a composition for clothing.

Examples of the hair cosmetic include a hair rinse, a hair conditioner, a hair treatment, a hair pack, a hair cream, a styling lotion, a styling mousse, a conditioning mousse, a hair mousse, a hair spray, a shampoo, a leave-on type conditioner, a permanent or basic hair coloring, and a perming agent.

In the hair cosmetic, oils and fats and silicones may be used alone or in combination with each other. In addition, if required, the hair cosmetic may also be appropriately compounded with conventional cationic surfactants such as mono- or di-(long-chain alkyl) quaternary ammonium salts or nonionic surfactants, humectants such as glycerol and urea, high-molecular substances such as cationic polymers, polysaccharides and polypeptides, α-hydroxycarboxylic acids, aromatic sulfonic acids, pigments, perfumery, propellants, solvents, chelating agents, pH controllers, antiseptic agents, anti-dandruff agents, etc.

The composition for clothing may be used as a fabric softener having an excellent softening property by appropriately compounding components compounded in the conventionally known fabric softeners. Examples of the components compounded in the fabric softeners include dimethyl distearyl ammonium chloride, silicone oils, a viscosity modifier, a storage stability improver, a pH controller, a hydrotrope agent, a pigment, a dye, a defoaming agent, a perfume, etc.

In the present invention, in addition to the above embodiments, there are described the following aspects concerning the production process.

<1> A surfactant composition comprising a compound represented by the formula (1) and a compound represented by the formula (2), a mass ratio of the compound represented by the formula (1) to the compound represented by the formula (2) [(1)/(2)] being from 65/35 to 75/25, preferably from 65/35 to 73/27, and more preferably from 65/35 to 70/30:

wherein $R^1$ is a linear alkyl group having 10 to 14 carbon atoms and preferably 12 to 14 carbon atoms; $[C_3H_6O_2]$ is a glycerol unit; n represents an average polymerization degree of $[C_3H_6O_2]$, and is a number of from 2.3 to 10, preferably from 2.3 to 6, and more preferably from 3 to 5; and a total content of a triglycerol monoalkyl ether, a tetraglycerol monoalkyl ether and a pentaglycerol monoalkyl ether in the compound represented by the formula (1) is 75% by mass or more, preferably 80% by mass or more, and more preferably from 85 to 98% by mass; and

wherein two $R^2$ groups are each independently a linear alkyl group having 10 to 14 carbon atoms and preferably 12 to 14 carbon atoms; $[C_3H_6O_2]$ is a glycerol unit; and m represents an average polymerization degree of $[C_3H_6O_2]$, and is a number of from 1 to 10, preferably from 3 to 7, and more preferably from 4 to 6.

<2> The surfactant composition according to the above aspect <1> further comprising a polyglycerol represented by the formula (3) in an amount of from 1 to 60% by mass, preferably from 10 to 50% by mass, more preferably from 20 to 45% by mass, and still more preferably from 20 to 40% by mass:

wherein $[C_3H_6O_2]$ is a glycerol unit; k represents an average polymerization degree of $[C_3H_6O_2]$, and is a number of from 1 to 10; and a total content of a diglycerol, a triglycerol and a tetraglycerol in the polyglycerol is 75% by mass or more.

<3> A process for producing the surfactant composition according to the above aspect <1> or <2>, comprising the following steps (I), (II) and (III):

Step (I): subjecting glycerol to dehydration condensation in the presence of an alkaline catalyst to obtain a glycerol polymer;

Step (II): removing glycerol, or glycerol and diglycerol from the glycerol polymer obtained in the step (I) to obtain a polyglycerol having a glycerol content of 5% by mass or less or having a glycerol content of 5% by mass or less and a diglycerol content of 40% by mass or less; and Step (III): subjecting the polyglycerol obtained in the step (II) to addition reaction with a glycidyl ether in the presence of a γ-alumina catalyst containing titanium in an amount of from 600 to 5000 ppm, preferably from 600 to 1300 ppm, and more preferably from 1000 to 1100 ppm, or an alkaline catalyst.

<4> The process for producing the surfactant composition according to the above aspect <3>, wherein in the step (III), the alkaline catalyst is used in an amount of more than 0.02% by mass and not more than 0.8% by mass, preferably from 0.03 to 0.7% by mass, more preferably from 0.03 to 0.6% by mass, still more preferably from 0.03 to 0.5% by mass, even still more preferably from 0.03 to 0.4% by mass, further even still more preferably from 0.03 to 0.3% by mass, and further even still more preferably from 0.04 to 0.2% by mass, and the addition reaction is conducted at a temperature of from 180 to 250° C., preferably from 180 to 240° C., more preferably from 185 to 230° C., and still more preferably from 190 to 230° C.

<5> The process for producing the surfactant composition according to the above aspect <3> or <4>, wherein the alkaline catalyst used in the step (I) is at least one compound selected from the group consisting of hydroxides, carbonates, bicarbonates and alkoxides of alkali metals or alkali earth metals, preferably at least one compound selected from the group consisting of hydroxides, carbonates and bicarbonates of alkali metals or alkali earth metals, and more preferably at least one compound selected from the group consisting of sodium hydroxide, potassium hydroxide, sodium carbonate, potassium carbonate and barium hydroxide.

<6> The process for producing the surfactant composition according to any one of the above aspects <3> to <5>, wherein an amount of the alkaline catalyst used in the step (I) is from 0.1 to 5 mol %, preferably from 0.1 to 3 mol %, more preferably from 0.2 to 2 mol %, and still more preferably from 0.2 to 1 mol % on the basis of the glycerol.

<7> A process for producing the surfactant composition according to the above aspect <1> or <2>, comprising the step of reacting an alcohol with glycidol in the presence of a simple metal salt of a rare earth element.

<8> The process for producing the surfactant composition according to the above aspect <7>, wherein the simple metal salt of a rare earth element is used in an amount of from 0.001 to 0.2 mol, preferably from 0.002 to 0.1 mol, and more preferably from 0.005 to 0.05 mol per 1 mol of the alcohol.

<9> An emulsifier composition comprising the surfactant composition as described in the above aspect <1> or <2>.

<10> A detergent composition comprising the surfactant composition as defined in the above aspect <1> or <2>.

<11> A process for producing a polyglycerol comprising the step of subjecting glycerol to dehydration condensation in the presence of an alkaline catalyst, wherein the glycerol has a carbonyl value of from 0.001 to 3.5 µmol/g, preferably from 0.01 to 3.5 µmol/g, more preferably from 0.1 to 3.5 µmol/g, still more preferably from 0.1 to 3.0 µmol/g, even still more preferably from 0.1 to 2.0 µmol/g, further even more preferably from 0.1 to 1.5 µmol/g, and further even still more preferably from 0.1 to 1.0 µmol/g.

<12> The process for producing a polyglycerol according to the above aspect <11>, wherein the glycerol has a conductivity of from 0 to 100 µS/cm, preferably from 0 to 50 µS/cm, more preferably from 0 to 30 µS/cm, still more preferably from 0 to 20 µS/cm, and even still more preferably from 0 to 10 µS/cm.

<13> The process for producing a polyglycerol according to the above aspect <11> or <12>, wherein after conducting a transesterification reaction step of subjecting oils and fats to transesterification reaction with an alcohol to obtain the glycerol, the step of subjecting the glycerol to dehydration condensation in the presence of the catalyst is conducted.

<14> The process for producing a polyglycerol according to the above aspect <13>, wherein the transesterification reaction step is conducted in the presence of a solid acid catalyst.

<15> The process for producing a polyglycerol according to the above aspect <14>, wherein the solid acid catalyst is at least one material selected from the group consisting of niobic acid, silica-alumina, silica-titania, silica-zirconia, titania-zirconia, aluminum phosphate, an aluminum orthophosphate catalyst, iron phosphate, aluminum sulfate, sulfate ion-carrying zirconia, sulfate ion-carrying titania, antimony pentafluoride-carrying silica-alumina, acid clay, kaolin, montmorillonite, a fluorinated sulfone resin, synthetic zeolite and a cation exchange resin.

<16> The process for producing a polyglycerol according to the above aspect <15>, wherein the solid acid catalyst is an aluminum orthophosphate catalyst, and preferably an alkyl phosphonic acid/aluminum phosphate composite catalyst obtained by introducing an alkyl group into an aluminum phosphate catalyst.

<17> The process for producing a polyglycerol according to any one of the above aspects <11> to <16>, wherein the glycerol is in the form of a crude glycerol.

<18> A process for producing diglycerol, including comprising the steps of producing the polyglycerol by the production process according to any one of the above aspects <11> to <17>, and then subjecting the resulting polyglycerol to distillation to obtain the diglycerol.

EXAMPLES

In the following Examples and Comparative Examples, whether or not the reaction was terminated was confirmed by elimination of a glycidyl ether or a glycidol as a raw material by gas chromatography (GC). In the following Production Examples and Comparative Production Examples, the conversion rate of glycerol was attained by quantitative determination of the glycerol by GC. The analyzer and analyzing conditions are shown below.

<Method of Measuring Carbonyl Value (COV) of Glycerol>

The carbonyl value of glycerol was measured by the same method as 4-DNPH method prescribed in The JOCS Standard Methods for the Analysis of Fats, Oils and Related Materials except for using ethanol in place of benzene as a solvent used therein (conducted on the basis of Standard Oils and Fats 2.5.4).

<Method of Measuring Conductivity of Glycerol>

The conductivity of a 50% glycerol aqueous solution prepared by adding ion-exchanged water to glycerol was measured at 20° C. using "Twin Cond B-137" available from Horiba, Ltd.

<Apparatus and Analyzing Conditions of Gas Chromatography>

A trimethylsilylating (ODS) reagent ("TMSI-H" available from G. L. Science K.K.) was added and mixed in a sample, and the resulting mixture was subjected to filtration to separate solids therefrom, and the obtained filtrate was subjected to quantitative determination by gas chromatography (GC) under the following conditions in which tetradecane (available from Wako Pure Chemical Industries, Ltd.) was used as an internal standard.

GC Apparatus: "HP 6850 Series" (available from Hewlett Packard Co.)

Column: "DB-1HT" (available from J & W Corp.; inner diameter: 0.25 m; length: 15 m; membrane thickness: 0.1 µm)

Carrier gas: He; 1.0 mL/min

The sample injection, detection and column temperature control was carried out according to any of the following conditions.

(Condition 1)
  Injection: 350° C.; split ratio: 1/50
  Detection: FID method; 350° C.
  Column temperature condition: 100° C. (held for 2 min) →raised at 10° C./min→350° C. (held for 10 min)

(Condition 2)
  Injection: 300° C.; split ratio: 1/50
  Detection: FID method; 300° C.
  Column temperature condition: 60° C. (held for 2 min) →raised at 10° C./min→350° C. (held for 5 min)

<Method of Measuring Average Polymerization Degree (n or m) of $[C_3H_6O_2]$>

The average polymerization degree (n or m) of $[C_3H_6O_2]$ was calculated from the following calculation formula (5)

based on the results of $^1$H-NMR measurement conducted by the following NMR apparatus under the following conditions.

Average Polymerization Degree ($n$ or $m$) of Glyceryl Ether=(Integrated Value of Protons in Glycerol Structure (3.4-4.0 ppm)/Integrated Value of One Proton in Alkyl Group (peak derived from methyl at 0.9 ppm in the case of a lauryl group)÷5) (5)

(Measuring Apparatus and Measuring Conditions of NMR)
NMR Apparatus: "Mercury 400BB" (400 MHz; available from Varian Inc.)
Observation Width: 6410.3 Hz
Pulse Width: 45 μs
Integration: 16 frequencies
Spin: 16 times
Data Point: 64 K
Pulse Delay Time: 10 s
Measuring Temperature: room temperature (25° C.)
Solvent: deuterated methanol or deuterated chloroform
<Method of Measuring Average Polymerization Degree (k) of Polyglycerol>
The average polymerization degree (k) of polyglycerol was calculated from the following calculation formula (6) based on the measured hydroxyl value (mg KOH/g) of the polyglycerol. The hydroxyl value was determined as follows. That is, hydroxyl groups contained in 1 g of a sample were acetylated with acetic anhydride and pyridine, and then a surplus of the acetic anhydride was hydrolyzed to subject the thus produced acetic acid to titration with potassium hydroxide.

Average Polymerization Degree ($k$) of Poyglycerol= (112200−18×[hydroxyl value]/(74.08×[hydroxyl value]−56100) (6)

<Method of Evaluating Hue>
The hue (Gardner value) of polyglycerol, etc., was measured and evaluated according to JIS K 0071-2. The lower the Gardner value becomes, the better the hue of the glycerol is.
In the case where the hue (Gardner value) is less than G1, the hue (APHA) of the polyglycerol, etc., was evaluated according to JIS K-3351 "Industrial glycerol". The lower the APHA value becomes, the better the hue of the glycerol is.

Production Example 1

Production of Polyglycerol

A reaction vessel was charged with glycerol (carbonyl value: 0.2 μmol/g; conductivity: 3 μS/cm; available from Kao Corp.) and potassium carbonate (available from Wako Pure Chemical Industries, Ltd.) in an amount of 0.5 mol % based on the glycerol, and the contents of the reaction vessel were subjected to dehydration condensation reaction at 240° C. at a vacuum degree of 66 kPa for 8.5 h. As a result of analyzing progress of the reaction by gas chromatography, it was confirmed that a conversion rate of the glycerol was 56%.
The reaction solution obtained after completion of the reaction was cooled and then diluted with ion-exchanged water, and after adding an ion exchange resin to the dilute solution, the resulting mixture was stirred at 40° C. for 5 h. The mixture was subjected to filtration to remove the ion exchange resin therefrom, and the resulting filtrate was heated to 145° C. while maintaining a vacuum degree of 467 Pa, and subjected to simple distillation to remove water therefrom.
Next, while maintaining a vacuum degree of 467 Pa, the obtained reaction solution was heated to 230° C. and subjected to simple distillation to remove the glycerol therefrom (the residual glycerol was present in an amount of 1% by weight based on a distillation residue). Then, the distillation residue from which the glycerol was removed, was heated to 193° C. at a vacuum degree of 0.13 Pa using a molecular distillation apparatus to distil off diglycerol therefrom, thereby obtaining a polyglycerol (average polymerization degree: 3.1; hydroxyl value: 1153 mg KOH/g) as a distillation residue.

Examples 1 to 4 and Comparative Examples 1 to 5

After mixing 370 g (1.48 mol) of the polyglycerol having an average polymerization degree of 3.1 obtained in Production Example 1 with 18.5 g (5% by mass based on the polyglycerol) of titanium-containing γ-alumina (available from Strem Chemicals Inc.; aluminum content: 49% by mass; titanium content: 1000 ppm; average particle size: 150 μm) at 120° C. while stirring, the resulting mixture was subjected to dehydration treatment under a reduced pressure of 0.05 kPa for 2 h. After completion of the dehydration treatment (water content in the reaction system: 0.05% by mass), the obtained reaction mixture was heated to 200° C., and 90 g (0.37 mol) of lauryl glycidyl ether was added thereto to initiate an addition reaction thereof under a pressure of 0.1 MPa. After 4 h from the initiation of the reaction, it was confirmed by GC that the lauryl glycidyl ether as the raw material was eliminated to thereby obtain a polyglycerol lauryl ether 1. The resulting final reaction product was purified by ODS silica gel column chromatography (eluent: EtOH/H$_2$O) to isolate a monoalkyl ether and a dialkyl ether.
As a result of analyzing a composition of each of the obtained monoalkyl ether and dialkyl ether by GC, it was confirmed that a total content of a triglycerol monoalkyl ether, a tetraglycerol monoalkyl ether and a pontaglycerol monoalkyl ether in the monoalkyl ether was 95% by mass (in terms of an area % in GC), an average polymerization degree (n) of [C$_3$H$_6$O$_2$] in the monoalkyl ether as calculated from NMR was 3.8, a total content of a tetraglycerol dialkyl ether, a pentaglycerol dialkyl ether and a hexaglycerol dialkyl ether in the dialkyl ether was 99% by mass (in terms of an area % in GC), and an average polymerization degree (m) of [C$_3$H$_6$O$_2$] in the dialkyl ether as calculated from NMR was 5.0. The thus isolated monoalkyl ether and dialkyl ether were mixed with each other at a mass ratio of 65/35 (Example 1 and Example 4), 70/30 (Example 2), 75/25 (Example 3), 100/0 (Comparative Example 1), 0/100 (Comparative Example 2), 55/45 (Comparative Example 3), 60/40 (Comparative Example 4) and 80/20 (Comparative Example 5). The resulting mixture was used to evaluate the following emulsification performance thereof.

Example 5

A monoalkyl ether (average polymerization degree n: 3.9) prepared by mixing the monoalkyl other used in Examples 1 to 4 with a tetraglycerol monolauryl ether ("SUN ETHER L-4" (tradename) available from Taiyo Kagaku Co., Ltd.) at a mass ratio of 50/50 was mixed with the dialkyl ether (average polymerization degree m: 5.0) used in Examples 1 to 4 at a mass ratio of 70/30. The resulting mixture was used to evaluate the following emulsification performance thereof.

Example 6

After mixing 50.03 g (0.20 mol) of the polyglycerol having an average polymerization degree of 3.1 obtained in Production Example 1 with 2.51 g (5% by mass based on the polyglycerol) of titanium-containing γ-alumina (available from Strem Chemicals Inc.; aluminum content: 49% by mass; titanium content: 1000 ppm; average particle size: 150 μm) at 120° C. while stirring, the resulting mixture was subjected to dehydration treatment under a reduced pressure of 0.05 kPa for 2 h. After completion of the dehydration treatment (water content in the reaction system: 0.05% by mass), the obtained reaction mixture was heated to 200° C., and 13.62 g (0.05 mol) of myristyl glycidyl ether was added dropwise thereto under a pressure of 0.1 MPa over 3 h. Upon completion of the dropwise addition, it was confirmed by GC that the myristyl glycidyl ether as the raw material was eliminated to thereby obtain a polyglycerol myristyl ether 1. The resulting final reaction product was purified by ODS silica gel column chromatography (eluent: EtOH/H$_2$O) to isolate a monoalkyl ether and a dialkyl ether.

As a result of analyzing a composition of each of the obtained monoalkyl ether and dialkyl ether by GC, it was confirmed that a total content of a triglycerol monoalkyl ether, a tetraglycerol monoalkyl ether and a pentaglycerol monoalkyl ether in the monoalkyl ether was 97% by mass (in terms of an area % in GC), an average polymerization degree (n) of [C$_3$H$_6$O$_2$] in the monoalkyl ether as calculated from NMR was 3.9, a total content of a tetraglycerol dialkyl ether, a pentaglycerol dialkyl ether and a hexaglycerol dialkyl ether in the dialkyl ether was 99% by mass (in terms of an area % in GC), and an average polymerization degree (m) of [C$_3$H$_6$O$_2$] in the dialkyl ether as calculated from NMR was 4.2. The thus isolated monoalkyl ether and dialkyl ether were mixed with each other at a mass ratio of 75/25. The resulting mixture was used to evaluate the following emulsification performance thereof.

Comparative Example 6

A monoalkyl ether (average polymerization degree n: 4.1) prepared by mixing the monoalkyl ether used in Examples 1 to 4 with a tetraglycerol monolauryl ether ("SUN ETHER L-4" (tradename) available from Taiyo Kagaku Co., Ltd.) at a mass ratio of 30/70 was mixed with the dialkyl ether (average polymerization degree m: 5.0) used in Examples 1 to 4 at a mass ratio of 70/30. The resulting mixture was used to evaluate the following emulsification performance thereof.

Comparative Examples 7 and 8

After mixing 80 g (0.20 mol) of a polyglycerol "#310" available from Sakamoto Yakuhin Kogyo Co., Ltd., with 4.2 g (5% by mass based on the polyglycerol) of γ-alumina (available from Strem Chemicals Inc.) at 120° C. while stirring, the resulting mixture was subjected to dehydration treatment under a reduced pressure of 0.05 kPa for 2 h. After completion of the dehydration treatment, the obtained reaction mixture was heated to 200° C., and 12 g (0.05 mol) of lauryl glycidyl ether was added thereto to initiate an addition reaction thereof. After 4 h from the initiation of the reaction, it was confirmed by GC that the lauryl glycidyl ether as the raw material was eliminated to thereby obtain a glycerol lauryl ether 2. The resulting final reaction product was purified by ODS silica gel column chromatography (eluent: EtOH/H$_2$O) to isolate a monoalkyl ether and a dialkyl ether.

As a result of analyzing a composition of each of the obtained monoalkyl ether and dialkyl ether by GC, it was confirmed that a total content of a triglycerol monoalkyl ether, a tetraglycerol monoalkyl ether and a pentaglycerol monoalkyl ether in the monoalkyl ether was 54% by mass (in terms of an area % in GC), an average polymerization degree (n) as calculated from NMR was 2.9, a total content of a tetraglycerol dialkyl ether, a pentaglycerol dialkyl ether and a hexaglycerol dialkyl ether in the dialkyl ether was 51% by mass (in terms of an area % in GC), and an average polymerization degree (m) as calculated from NMR was 3.1. The thus isolated monoalkyl ether and dialkyl ether were mixed with each other at a mass ratio of 75/25 (Comparative Example 7) and 80/20 (Comparative Example 8). The resulting mixture was used to evaluate the following emulsification performance thereof.

Comparative Example 9

After mixing 247.8 g (0.99 mol) of the polyglycerol having an average polymerization degree of 3.1 obtained in Production Example 1 with 12.4 g (5% by mass based on the polyglycerol) of γ-alumina (available from Strem Chemicals Inc.) at 120° C. while stirring, the resulting mixture was subjected to dehydration treatment under a reduced pressure of 0.05 kPa for 2 h. After completion of the dehydration treatment, the obtained reaction mixture was heated to 200° C., and 92.0 g (0.49 mol) of 2-ethylhexyl glycidyl ether was added thereto to initiate an addition reaction thereof. After 4 h from the initiation of the reaction, it was confirmed by GC that the lauryl glycidyl ether as the raw material was eliminated to thereby obtain a polyglycerol 2-ethylhexyl ether 1. The resulting final reaction product was purified by ODS silica gel column chromatography (eluent: EtOH/H$_2$O) to isolate a monoalkyl other and a dialkyl ether.

As a result of analyzing a composition of each of the obtained monoalkyl ether and dialkyl ether by GC, it was confirmed that a total content of a triglycerol monoalkyl ether, a tetraglycerol monoalkyl ether and a pentaglycerol monoalkyl ether in the monoalkyl ether was 94% by mass (in terms of an area % in GC), an average polymerization degree (n) as calculated from NMR was 3.5, a total content of a tetraglycerol dialkyl ether, a pentaglycerol dialkyl ether and a hexaglycerol dialkyl ether in the dialkyl ether was 89% by mass (in terms of an area % in GC), and an average polymerization degree (m) as calculated from NMR was 4.6. The thus isolated monoalkyl ether and dialkyl ether were mixed with each other at a mass ratio of 75/25. The resulting mixture was used to evaluate the following emulsification performance thereof.

Comparative Examples 10 to 13

After mixing 135.24 g (0.5 mol) of 1-octadecanol with 2.9 g (5 mmol) of trifluoromethanesulfonic acid lanthanum salt (available from Tokyo Chemical Industry Co., Ltd.) at 90° C. in a nitrogen atmosphere, 48.16 g (2 mol) of glycidol (available from Kanto Chemical Co., Inc.) was added dropwise thereto over 3 h to initiate an addition reaction thereof. After 4 h from the initiation of the reaction, the reaction was terminated, thereby obtaining a polyglycerol octadecyl ether 1. As a result of analyzing a composition of the obtained polyglycerol octadecyl ether 1 by GC, it was confirmed that a total content of a triglycerol monoalkyl ether, a tetraglycerol monoalkyl ether and a pentaglycerol monoalkyl ether therein was 39% by mass (in terms of an area % in GC), and an average polymerization degree (n) as calculated from NMR was 3.9. The resulting product was used to evaluate the following emulsification performance thereof.

<Test for Evaluation of Emulsifying Power>

The surfactant compositions obtained in the respective Examples were subjected to emulsification test by the following method and conditions.

(1) Emulsification Test Method 1

A 10 mL graduated test tube (available from Iwaki & Co., Ltd.) was filled with 0.2 g of the surfactant composition and 0.04 g of a polyglycerol having an average polymerization degree of 3.1 (except for Example 4), and 2.8 g of distilled water was added to the test tube to dissolve the contents of the test tube therein. Next, 2.0 g of a silicone oil ("KF-96A-6cs" available from Shin-Etsu Chemical Co., Ltd.) as an oil to be emulsified was added to the thus obtained solution, and the resulting mixture was stirred at room temperature using a pencil mixer ("1-299-02" (product number) available from ASONE Corp.; equipped with a stirring bar 2-type; rotating number: 7000 rpm) for 1 min. In Example 5, the same measurement as described above was conducted except for using a rapeseed oil (available from Yamakei Sangyo K.K.) and "ESTEMOL N-01" (available from Nissin OilliO Group, Ltd.; diester of neopentyl glycol and a medium-chain linear fatty acid) in place of the silicone oil. An amount of a layer of water released from the resulting emulsion after the elapse of 2 h was measured to evaluate an emulsification performance of the surfactant composition.

(2) Evaluation of Emulsifying Power

Under the above conditions, an emulsifying power of the surfactant composition was calculated from the amount of water released from the emulsion after the elapse of 2 h according to the following formula to evaluate an emulsifying power thereof.

Emulsifying Power (%)=[(amount of water charged−amount of water released)(mL)/amount of water charged (mL)]×100

The results of evaluation of an emulsifying power of the respective surfactant compositions against the silicone oil are shown in Table 1.

Meanwhile, in Example 5, the emulsification performance of the surfactant composition was evaluated by the same method as described above except for using a rapeseed oil and the above "ESTEMOL N-01" as an oil to be emulsified in place of the silicone oil. The emulsifying power of the surfactant composition calculated from the amount of water released after the elapse of 2 h was 79% for the rapeseed oil and 71% for the "ESTEMOL N-01".

(3) Emulsification Test Method 2

A 10 mL graduated test tube (available from Iwaki & Co., Ltd.) was filled with 0.5 g of the surfactant composition and 0.02 g of a polyglycerol having an average polymerization degree of 3.1 obtained in Production Example 1 (in Comparative Examples 12 and 13, no polyglycerol was used), and 1.4 g of distilled water was added to the test tube to dissolve the contents of the test tube therein. Next, 1.0 g of a rapeseed oil (available from Yamakei Sangyo K.K.) or "COSMOL 41V" (available from Nissin OilliO Group, Ltd.; monoester of diglycol and a methyl-branched type isostearic acid) as an oil to be emulsified was added to the thus obtained solution, and the resulting mixture was stirred at room temperature using a pencil mixer ("1-299-02" (product number) available from ASONE Corp.; equipped with a stirring bar 2-type; rotating number: 7000 rpm) for 1 min. An amount of a layer of water released from the 16 resulting emulsion after the elapse of 2 h was measured to evaluate an emulsification performance of the surfactant composition. Meanwhile, the emulsifying power of the surfactant composition was calculated from the same calculation formula as described in the above (2). In addition, the fluidity of the resulting emulsion was evaluated as follows. That is, after preparation of the emulsion, the test tube was turned upside down and held in this state to examine whether or not the emulsion fell down along an inner wall surface of the test tube within 10 s. In the case where the emulsion fell down within 10 s, the emulsion was evaluated as being "fluidizable", whereas in the case where the emulsion was held in the test tube as such without falling down within 10 s, the emulsion was evaluated as being "not fluidizable". Incidentally, in the case where the emulsion had no fluidity, the condition of water released from the emulsion was visually unobservable, so that it was not possible to measure an emulsifying power of the surfactant composition. The evaluation results are shown in Table 2.

TABLE 1

| | Examples | | | | | | Comparative Examples | | | | | | | | |
|---|---|---|---|---|---|---|---|---|---|---|---|---|---|---|---|
| | 1 | 2 | 3 | 4 | 5 | 6 | 1 | 2 | 3 | 4 | 5 | 6 | 7 | 8 | 9 |
| Monoalkyl ether (1)/Dialkyl ether (2) (mass ratio) | 65/35 | 70/30 | 75/25 | 65/35 | 70/30 | 75/25 | 100/0 | 0/100 | 55/45 | 60/40 | 80/20 | 70/30 | 75/25 | 80/20 | 75/25 |
| Monoalkyl ether (1) | | | | | | | | | | | | | | | |
| $R^1$ alkyl chain | C12 | C12 | C12 | C12 | C12 | C14 | C12 | C12 | C12 | C12 | C12 | C12 | C12 | C12 | C8 |
| Total content (mass %)*[1] | 95 | 95 | 95 | 95 | 78 | 97 | 95 | — | 95 | 95 | 95 | 60 | 54 | 54 | 94 |
| n | 3.8 | 3.8 | 3.8 | 3.8 | 3.9 | 3.9 | 3.8 | 3.8 | 3.8 | 3.8 | 3.8 | 4.1 | 2.9 | 2.9 | 3.5 |
| Dialkyl ether (2) | | | | | | | | | | | | | | | |
| $R^2$ alkyl chain | C12 | C12 | C12 | C12 | C12 | C14 | C12 | C12 | C12 | C12 | C12 | C12 | C12 | C12 | C8 |
| Total content (mass %)*[2] | 99 | 99 | 99 | 99 | 99 | 99 | — | 99 | 99 | 99 | 99 | 99 | 51 | 51 | 89 |
| m | 5.0 | 5.0 | 5.0 | 5.0 | 5.0 | 4.2 | — | 5.0 | 5.0 | 5.0 | 5.0 | 5.0 | 3.1 | 3.1 | 4.6 |
| Polyglycerol content (mass %) | 20 | 20 | 20 | 0 | 20 | 20 | 20 | 20 | 20 | 20 | 20 | 20 | 20 | 20 | 20 |
| Emulsifying power (%) | 100 | 100 | 96 | 100 | 89 | 93 | 29 | 0 | 29 | 36 | 54 | 71 | 36 | 29 | 11 |

Note
*[1]Total content of triglycerol monoalkyl ether, tetraglycerol monoalkyl ether and pentaglycerol monoalkyl ether.
*[2]Total content of tetraglycerol dialkyl ether, pentaglycerol dialkyl ether and hexaglycerol dialkyl ether.

TABLE 2

|  | Examples | Comparative Examples | | | |
| --- | --- | --- | --- | --- | --- |
|  | 1 | 10 | 11 | 12 | 13 |
| Oil to be emulsified | Rapeseed oil | Ester oil ("COSMOL 41V") | Rapeseed oil | Ester oil ("COSMOL 41V") | Rapeseed oil | Ester oil ("COSMOL 41V") |
| Monoalkyl ether (1)/ Dialkyl ether (2) (mass ratio) | 65/35 | 65/35 | 100/0 | 100/0 | 100/0 | 100/0 |
| Monoalkyl ether (1) |  |  |  |  |  |  |
| $R^1$ alkyl chain | C12 | C12 | C18 | C18 | C18 | C18 |
| Total content, (mass %)*1 | 95 | 95 | 39 | 39 | 39 | 39 |
| n | 3.8 | 3.8 | 3.9 | 3.9 | 3.9 | 3.9 |
| Dialkyl ether (2) |  |  |  |  |  |  |
| $R^2$ alkyl chain | C12 | C12 | — | — | — | — |
| Total content (mass %)*2 | 99 | 99 | — | — | — | — |
| m | 5.0 | 5.0 | — | — | — | — |
| Polyglycerol content (mass %) | 20 | 20 | 20 | 20 | 0 | 0 |
| Fluidity | Fluidizable | Fluidizable | Not fluidizable Solidified | Not fluidizable Solidified | Not fluidizable Solidified | Not fluidizable Solidified |
| Emulsifying power (%) | 100 | 100 |  |  |  |  |

Note
*1 Total content of triglycerol monoalkyl ether, tetraglycerol monoalkyl ether and pentaglycerol monoalkyl ether.
*2 Total content of tetraglycerol dialkyl ether, pentaglycerol dialkyl ether and hexaglycerol dialkyl ether.

Production Examples 2-1 to 2-4 and Comparative Production Examples 2-1 and 2-2 (Production of Polyglycerol or Diglycerol)

Production Example 2-1 (Production of Polyglycerol)

A 200 mL four-necked flask was charged with 100.43 g (1.09 mol) of glycerol (COV: 0.2 mol/g; APHA: 5) and 0.76 g (5.5 mmol) of potassium carbonate (available from Wako Pure Chemical Industries, Ltd.). After reducing an inside pressure of the flask to 67 kPa, the contents of the flask were heated to 240° C. and subjected to dehydration condensation reaction for 7.5 h while removing water produced by the reaction.

As a result of analyzing progress of the reaction by gas chromatography, it was confirmed that a conversion rate of the glycerol was 49%, and the resulting polyglycerol exhibited a hue represented by a Gardner value of less than 1 and an APHA value of 200. The results are shown in Table 3.

Production Example 2-2 (Production of Polyglycerol)

The dehydration condensation reaction was conducted by the same method as in Production Example 2-1 except for using 100.71 g (1.09 mol) of glycerol having a COV of 3.1 μmol/g and an APHA value of 5. The results are shown in Table 3.

Production Example 2-3 (Production of Polyglycerol)

Ethyl phosphonic acid, 85% of orthophosphoric acid and aluminum nitrate (nonahydrate) were weighed in amounts of 9.9 g, 27.7 g and 112.5 g, respectively, and dissolved in 1000 g of water. An ammonia aqueous solution was added dropwise into the resulting mixed solution at room temperature (25° C.) to raise a pH value thereof to 5. In the course of the dropwise addition, a gel-like white precipitate was produced. The obtained reaction solution was subjected to filtration to separate the precipitate therefrom, and the resulting precipitate was washed with water, dried at 110° C. for 5 h, and then pulverized into particles of 60 mesh or smaller. The thus pulverized catalyst was mixed with 10% of alumina sol, and the resulting mixture was extrusion-molded into 2.5 mmφ and calcined at 250° C. for 3 h to obtain a solid acid catalyst in the form of a molded catalyst.

Using a fixed bed reaction vessel filled with the above molded catalyst, a coconut oil and methanol were subjected to transesterification reaction (reaction temperature: 180° C.; reaction pressure: 4.0 MPa; LHSV: 0.42; methanol/coconut oil (molar ratio)=10), and then methanol was recovered from the obtained reaction solution by an ordinary method, thereby obtaining a crude glycerol.

The dehydration condensation reaction was conducted by the same method as in Production Example 2-1 except for using 600 g (6.51 mol) of the thus obtained crude glycerol (COV: 1.5 μmol/g; Gardner value: G2-G3) and 4.5 g (32 mmol) of potassium carbonate (available from Wako Pure Chemical Industries, Ltd.). The results are shown in Table 3.

Comparative Production Example 2-1

The dehydration condensation reaction was conducted by the same method as in Production Example 2-1 except for using 100.86 g (1.10 mol) of glycerol (COV: 11.6 μmol/g; APHA value: 5). The results are shown in Table 3.

TABLE 3

|  |  |  | Production Example 2-1 | Production Example 2-2 | Production Example 2-3 | Comparative Production Example 2-1 |
|---|---|---|---|---|---|---|
| Raw glycerol | Hue | Gardner value | <1 | <1 | 2-3 | <1 |
|  |  | (APHA value) | (5) | (5) | (—) | (5) |
|  | Carbonyl value | µmol/g | 0.2 | 3.1 | 1.5 | 11.6 |
|  | Conductivity | µS/cm | 3 | 6 | 5 | 14 |
| Dehydration condensation reaction | Catalyst |  | Potassium carbonate | Potassium carbonate | Potassium carbonate | Potassium carbonate |
|  | Temperature | °C. | 240 | 240 | 240 | 240 |
|  | Pressure | kPa | 67 | 67 | 67 | 67 |
|  | Reaction time | h | 7.5 | 7.5 | 7.5 | 7.5 |
| Conversion rate of glycerol |  | % | 49 | 47 | 55 | 51 |
| Hue of polyglycerol |  | Gardner value | <1 | 1 | 2-3 | 8 |
|  |  | (APHA value) | (200) | (—) | (—) | (—) |

Production Example 2-4 (Production of Diglycerol)

Dehydration Condensation Reaction Step

A 1000 mL four-necked flask was charged with 600 g (6.51 mol) of the crude glycerol (COV: 1.5 µmol/g; conductivity: 5 µS/cm) obtained in Production Example 2-3 and 4.5 g (32 mmol) of potassium carbonate (available from Wako Pure Chemical Industries, Ltd.), and the contents of the flask were subjected to dehydration condensation reaction under the same conditions as used in Production Example 2-1. As a result of analyzing progress of the reaction by gas chromatography, it was confirmed that a conversion rate of the glycerol was 55% (yield: 559 g).

[Neutralization Step and Distillation Step (I) of Glycerol]

After completion of the reaction, the resulting reaction solution was cooled to 100° C. or lower, and sulfuric acid was added thereto to neutralize the reaction solution to a pH value of 7.

Next, while maintaining a vacuum degree of 40 Pa, the reaction solution was heated to 190° C. and subjected to simple distillation to distil off the glycerol therefrom. The thus recovered glycerol (yield: 230 g) exhibited a hue (Gardner value) of less than G1 and a hue (APHA) of 40.

[Distillation Step (II) of Diglycerol]

The distillation residue from which the glycerol was removed was subjected to distillation using a thin-film type distillation apparatus (wiper type) at a vacuum degree of 20 Pa at a temperature of 240° C. to distil off diglycerol therefrom. The resulting purified diglycerol (yield: 142 g) exhibited a hue (Gardner value) of less than G1 and a hue (APHA) of 80.

Comparative Production Example 2-2

A 1000 mL four-necked flask was charged with 532 g (5.78 mol) of a crude glycerol (COV: 3.8 µmol/g; conductivity: 270 µS/cm) and 4.0 g (29 mmol) of potassium carbonate (available from Wako Pure Chemical Industries, Ltd.), and the contents of the flask were subjected to dehydration condensation reaction step under the same conditions as used in Production Example 2-4 to obtain a crude diglycerol. As a result, it was confirmed that a conversion rate of glycerol in the resulting crude diglycerol was 48% (yield: 516 g).

After completion of the reaction, the resulting reaction solution was subjected to distillation under the same conditions as used in the distillation step of the glycerol in Production Example 2-4 to distil off and remove the unreacted glycerol therefrom. The thus recovered glycerol (yield: 273 g) exhibited a hue (Gardner value) of G3.

Next, the distillation residue from which the glycerol was removed was subjected to distillation under the same conditions as used in the distillation step of the diglycerol in Production Example 2-4 to obtain a purified diglycerol. The resulting purified diglycerol (yield: 106 g) exhibited a hue (Gardner value) of G6-G7.

TABLE 4

|  |  |  | Production Example 2-4 | Comparative Production Example 2-2 |
|---|---|---|---|---|
| Raw glycerol | Carbonyl value | µmol/g | 1.5 | 3.8 |
|  | Conductivity | µS/cm | 5 | 270 |
| Dehydration condensation reaction | Catalyst | — | Potassium carbonate | Potassium carbonate |
|  | Temperature | °C. | 240 | 240 |
|  | Pressure | kPa | 67 | 67 |
|  | Time | h | 7.5 | 7.5 |
| Conversion rate of glycerol |  | % | 55 | 48 |
| Neutralization | Neutralization agent | — | Sulfuric acid | Sulfuric acid |
| Distillation I | Temperature | °C. | 190 | 190 |
|  | Pressure | Pa | 40 | 40 |
| Distillation II | Temperature | °C. | 240 | 240 |
|  | Pressure | Pa | 20 | 20 |
| Hue of diglycerol |  | Gardner value | <1 | 6-7 |
|  |  | (APHA value) | (80) | (—) |

INDUSTRIAL APPLICABILITY

The surfactant composition of the present invention can exhibit an extremely high emulsifying power against silicone oils generally used in cosmetics or perfumery, and detergents. In addition, the surfactant composition can also exhibit an extremely high emulsifying power against hydrocarbon-based oil-soluble substances generally used in cosmetics or perfumery, and detergents. Therefore, the surfactant composition of the present invention can be used in the extensive applications as skin cosmetics, hair cosmetics, emulsifier compositions for clothing, and detergent compositions.

The invention claimed is:

1. A surfactant composition comprising a compound represented by the formula (1) and a compound represented by the formula (2), a mass ratio of the compound represented by the formula (1) to the compound represented by the formula (2) [(1)/(2)] being from 65/35 to 75/25:

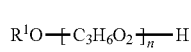
(1)

wherein $R^1$ is a linear alkyl group having 10 to 14 carbon atoms; $[C_3H_6O_2]$ is a glycerol unit; n represents an average polymerization degree of $[C_3H_6O_2]$, and is a number of from 2.3 to 10; and a total content of a triglycerol monoalkyl ether, a tetraglycerol monoalkyl ether and a pentaglycerol monoalkyl ether in the compound represented by the formula (1) is 75% by mass or more; and

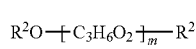
(2)

wherein two $R^2$ groups are each independently a linear alkyl group having 10 to 14 carbon atoms; $[C_3H_6O_2]$ is a glycerol unit; and m represents an average polymerization degree of $[C_3H_6O_2]$, and is a number of from 1 to 10.

2. The surfactant composition according to claim 1 further comprising a polyglycerol represented by the formula (3) in an amount of from 1 to 60% by mass:

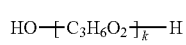
(3)

wherein $[C_3H_6O_2]$ is a glycerol unit; k represents an average polymerization degree of $[C_3H_6O_2]$, and is a number of from 1 to 10; and a total content of a diglycerol, a triglycerol and a tetraglycerol in the polyglycerol is 75% by mass or more.

3. A process for producing the surfactant composition according to claim 1, comprising the steps (I), (II) and (III):
Step (I): subjecting glycerol to dehydration condensation in the presence of an alkaline catalyst to obtain a glycerol polymer;
Step (II): removing glycerol, or glycerol and diglycerol from the glycerol polymer obtained in the step (I) to obtain a polyglycerol having a glycerol content of 5% by mass or less or having a glycerol content of 5% by mass or less and a diglycerol content of 40% by mass or less; and
Step (III): subjecting the polyglycerol obtained in the step (II) to addition reaction with a glycidyl ether in the presence of a γ-alumina catalyst containing titanium in an amount of from 600 to 5000 ppm, or an alkaline catalyst.

4. The process for producing the surfactant composition according to claim 3, wherein in the step (III), the alkaline catalyst is used in an amount of more than 0.02% by mass and not more than 0.8% by mass on the basis of the polyglycerol, and the addition reaction is conducted at a temperature of from 180 to 250° C.

5. A process for producing the surfactant composition according to claim 1, comprising a step of reacting an alcohol with glycidol in the presence of a simple metal salt of a rare earth element.

6. An emulsifier composition comprising the surfactant composition according to claim 1.

7. A detergent composition comprising the surfactant composition according to claim 1.

8. The surfactant composition according to claim 1, wherein the mass ratio of the compound represented by the formula (1) to the compound represented by the formula (2) [(1)/(2)] is from 65/35 to 73/27.

9. The surfactant composition according to claim 1, wherein the mass ratio of the compound represented by the formula (1) to the compound represented by the formula (2) [(1)/(2)] is from 65/35 to 70/30.

10. The surfactant composition according to claim 2, wherein the surfactant composition comprises the polyglycerol represented by the formula (3) in an amount of from 10 to 50% by mass.

11. The surfactant composition according to claim 2, wherein the surfactant composition comprises the polyglycerol represented by the formula (3) in an amount of from 20 to 40% by mass.

12. The process for producing the surfactant composition according to claim 3, wherein in the step (III), the polyglycerol obtained in the step (II) is subjected to addition reaction with the glycidyl ether in the presence of the γ-alumina catalyst containing titanium in an amount of from 1000 to 1100 ppm, or the alkaline catalyst.

13. The process for producing the surfactant composition according to claim 3, wherein in the step (III), the alkaline catalyst is used in an amount of from 0.04 to 0.2% by mass on the basis of the polyglycerol, and the addition reaction is conducted at a temperature of from 190 to 230° C.

14. The process for producing the surfactant composition according to claim 3, wherein the alkaline catalyst used in the step (I) is at least one compound selected from the group consisting of sodium hydroxide, potassium hydroxide, sodium carbonate, potassium carbonate and barium hydroxide.

15. The process for producing the surfactant composition according to claim 5, wherein the simple metal salt of the rare earth element is used in an amount of from 0.001 to 0.2 mol per 1 mol of the alcohol.

16. The process for producing the surfactant composition according to claim 5, wherein the simple metal salt of the rare earth element is used in an amount of from 0.002 to 0.1 mol per 1 mol of the alcohol.

17. The process for producing the surfactant composition according to claim 5, wherein the simple metal salt of the rare earth element is used in an amount of from 0.005 to 0.05 mol per 1 mol of the alcohol.

* * * * *